United States Patent
Cohen et al.

(10) Patent No.: US 10,918,310 B2
(45) Date of Patent: Feb. 16, 2021

(54) FAST ANATOMICAL MAPPING (FAM) USING VOLUME FILLING

(71) Applicant: BIOSENSE WEBSTER (ISRAEL) LTD., Yokneam (IL)

(72) Inventors: Assaf Cohen, Kiryat Bialik (IL); Ido Ilan, Yoqneam (IL); Itai Doron, Katsir (IL); Fady Massarwi, Baka al Gharbiyya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 511 days.

(21) Appl. No.: 15/861,413

(22) Filed: Jan. 3, 2018

(65) Prior Publication Data
US 2019/0200901 A1    Jul. 4, 2019

(51) Int. Cl.
| | | |
|---|---|---|
| A61B 5/107 | (2006.01) | |
| A61B 5/06 | (2006.01) | |
| A61B 5/042 | (2006.01) | |
| A61B 34/20 | (2016.01) | |
| A61B 5/00 | (2006.01) | |
| A61B 90/00 | (2016.01) | |
| A61B 34/10 | (2016.01) | |
| A61B 5/02 | (2006.01) | |

(52) U.S. Cl.
CPC ............ *A61B 5/1076* (2013.01); *A61B 5/02* (2013.01); *A61B 5/0422* (2013.01); *A61B 5/062* (2013.01); *A61B 5/065* (2013.01); *A61B 5/1073* (2013.01); *A61B 5/6852* (2013.01); *A61B 5/6857* (2013.01); *A61B 5/6859* (2013.01); *A61B 5/7278* (2013.01); *A61B 5/743* (2013.01); *A61B 34/10* (2016.02); *A61B 34/20* (2016.02); *A61B 90/37* (2016.02); *A61B 2034/105* (2016.02); *A61B 2034/2051* (2016.02); *A61B 2034/2061* (2016.02)

(58) Field of Classification Search
CPC ....... A61B 5/1076; A61B 34/10; A61B 34/20; A61B 90/37; A61B 5/02; A61B 5/0422; A61B 5/062; A61B 5/065; A61B 5/1073; A61B 5/6852; A61B 5/6857; A61B 5/6859; A61B 5/7278; A61B 5/743
USPC ........................................................ 600/587
See application file for complete search history.

(56) References Cited

U.S. PATENT DOCUMENTS

| | | |
|---|---|---|
| 5,391,199 A | 2/1995 | Ben-Haim |
| 6,239,724 B1 | 5/2001 | Doron et al. |
| 6,301,496 B1 | 10/2001 | Reisfeld |
| 6,332,089 B1 | 12/2001 | Acker et al. |

(Continued)

FOREIGN PATENT DOCUMENTS

| | | |
|---|---|---|
| EP | 3167835 | 5/2017 |
| WO | WO 96/05768 A1 | 2/1996 |

OTHER PUBLICATIONS

Pending U.S. Appl. No. 15/610,865, filed Jun. 1, 2017.
European Search Report dated May 29, 2019 from corresponding European Patent Application No. 19150087.5.

*Primary Examiner* — Daniel L Cerioni

(57) ABSTRACT

A method includes receiving one or more signals indicative of a position of a distal-end assembly of a medical probe within an organ of a patient. Based on the received signals, an inner volume that is confined within the distal-end assembly is determined. An anatomical map of the organ is updated, to denote the inner volume of the distal-end assembly as belonging to an interior of the organ.

12 Claims, 3 Drawing Sheets

(56) References Cited

U.S. PATENT DOCUMENTS

| | | |
|---|---|---|
| 6,484,118 B1 | 11/2002 | Govari |
| 6,618,612 B1 | 9/2003 | Acker et al. |
| 6,690,963 B2 | 2/2004 | Ben-Haim et al. |
| 7,756,576 B2 | 7/2010 | Levin |
| 7,848,787 B2 | 12/2010 | Osadchy |
| 7,848,789 B2 | 12/2010 | Govari et al. |
| 7,869,865 B2 | 1/2011 | Govari et al. |
| 8,456,182 B2 | 6/2013 | Bar-Tal et al. |
| 8,532,738 B2 | 9/2013 | Zino |
| 2002/0065455 A1 | 5/2002 | Ben-Haim et al. |
| 2003/0120150 A1 | 6/2003 | Govari |
| 2004/0068178 A1 | 4/2004 | Govari |
| 2006/0178587 A1 | 8/2006 | Khoury |
| 2009/0148012 A1* | 6/2009 | Altmann ............... A61B 8/4488 382/128 |
| 2010/0106154 A1 | 4/2010 | Harley et al. |
| 2010/0168550 A1 | 7/2010 | Byrd et al. |
| 2011/0160569 A1 | 6/2011 | Cohen et al. |
| 2014/0095105 A1 | 4/2014 | Koyrakh et al. |
| 2015/0238275 A1* | 8/2015 | Kung .................. A61B 5/1076 600/424 |

\* cited by examiner

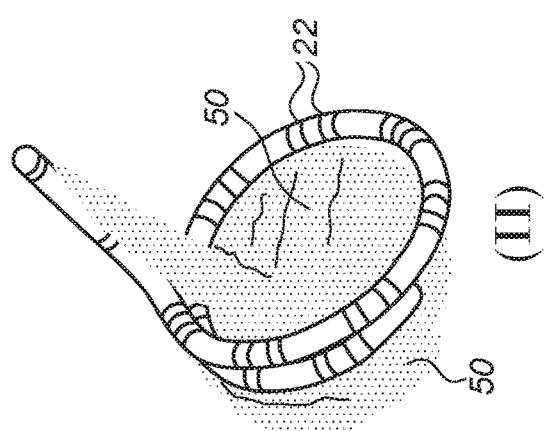
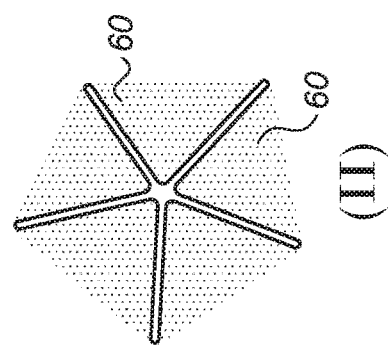
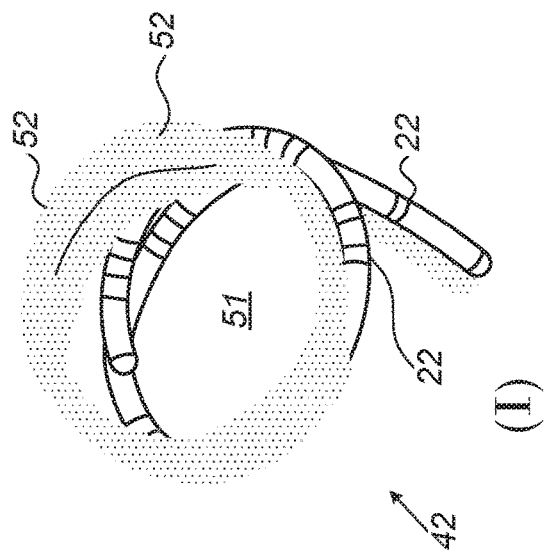
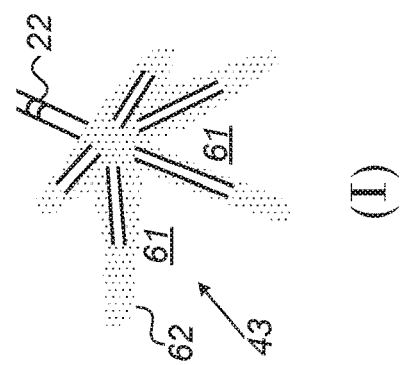
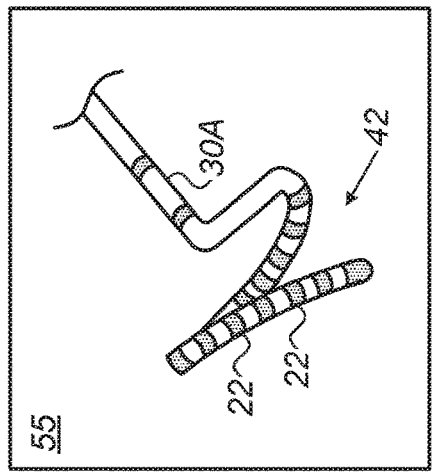
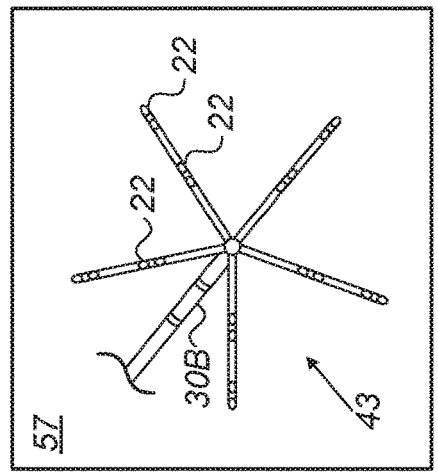
FIG. 2A
FIG. 2B

FAST ANATOMICAL MAPPING (FAM) USING VOLUME FILLING

FIELD OF THE INVENTION

The present invention relates generally to anatomical mapping, and particularly to methods and systems for cardiac anatomical mapping.

BACKGROUND OF THE INVENTION

Anatomical mapping of cardiac cavities is often employed during invasive cardiac procedures. For example, U.S. Patent Application Publication 2010/0168550 describes a system for constructing multiple modeled shells indicative of the geometry and/or volume of a heart chamber. The system is configured to collect a plurality of location data points as an electrode is swept within the chamber. Each of the collected data points has an associated measured cardiac phase at which such point was acquired. The system is configured to segregate the collected electrode locations into sets based on the phase. Each set is characterized by a particular, associated phase of its constituent electrode locations. The system is configured to generate, for each set, a respective shell model that will represent the chamber at the associated phase. The shells, once constructed, may be used for, or in connection with, a variety of diagnostic, mapping, and/or therapeutic procedures. The system is also configured to verify that the electrode is in contact with the heart tissue before using the collected data point in the shell construction (e.g., using a phase angle parameter to verify contact).

As another example, U.S. Patent Application Publication 2006/0178587 describes systems and methods for calibrating calculations based on catheter-originated measurements. One embodiment comprises a method for calibrating volume calculations for a fluid-filled cavity, such as a heart chamber. In this method, a first catheter configured to measure electrical characteristics and a second catheter configured to measure geometric characteristics are inserted into a fluid-filled cavity. Electrical characteristics of the fluid-filled cavity are measured with the first catheter and geometric characteristics of the cavity are measured with the second catheter. A volume segment is determined based on the measured geometric characteristics of the cavity, and a corresponding volume segment is determined based on the measured electrical characteristics of the cavity. Because the geometric calculation of the volume is known to be more accurate, the volume calculation based on the electrical measurements is adjusted (calibrated) to match the geometric calculation U.S. Patent Application Publication 2014/0095105 describes an algorithm to correct and/or scale an electrical current-based coordinate system that can include the determination of one or more global transformation or interpolation functions and/or one or more local transformation functions. The global and local transformation functions can be determined by calculating a global metric tensor and a number of local metric tensors. The metric tensors can be calculated based on pre-determined and measured distances between closely-spaced sensors on a catheter.

SUMMARY OF THE INVENTION

An embodiment of the present invention provides a method including receiving one or more signals indicative of a position of a distal-end assembly of a medical probe within an organ of a patient. Based on the received signals, an inner volume that is confined within the distal-end assembly is determined. An anatomical map of the organ is updated to denote the inner volume of the distal-end assembly as belonging to an interior of the organ.

In some embodiments, the method includes calculating, based on the received signals, positions of one or more sensors coupled to the distal-end assembly, and deriving the inner volume from the positions of the sensors.

In some embodiments, the method includes calculating the inner volume based on the positions of the sensors and on a known geometrical shape of the distal-end assembly.

In an embodiment, the method includes verifying whether the distal-end assembly is deformed, and denoting the inner volume of the distal-end assembly as belonging to the interior of the organ only when the distal-end assembly is not deformed.

In another embodiment, the method includes, in response to detecting that the distal-end assembly is deformed, updating the anatomical map to denote only at least part of an external surface of the distal-end assembly as belonging to the interior of the organ.

In some embodiments, the method includes verifying whether a surface associated with the distal-end assembly is planar.

In some embodiments, the method includes verifying whether an actual geometrical shape of the distal-end assembly deviates from a known un-deformed geometrical shape of the distal-end assembly.

In an embodiment, the method includes verifying whether the distal-end assembly is deformed includes identifying mechanical contact between the distal-end assembly and a surface of the organ.

There is additionally provided, in accordance with an embodiment of the present invention, an apparatus including an electrical interface and a processor. The processor is configured to receive via the electrical interface one or more signals indicative of a position of a distal-end assembly of a medical probe within an organ of a patient. Based on the received signals, the processor is configured to determine an inner volume that is confined within the distal-end assembly, and to update an anatomical map of the organ to denote the inner volume of the distal-end assembly as belonging to an interior of the organ.

The present invention will be more fully understood from the following detailed description of the embodiments thereof, taken together with the drawings in which:

BRIEF DESCRIPTION OF THE DRAWINGS

FIGS. 2A and 2B are volume rendered maps of cavity anatomy mapped by Lasso® and Pentaray® mapping catheters, respectively, in accordance with embodiments of the present invention.

DETAILED DESCRIPTION OF EMBODIMENTS

Overview

Figure 1:
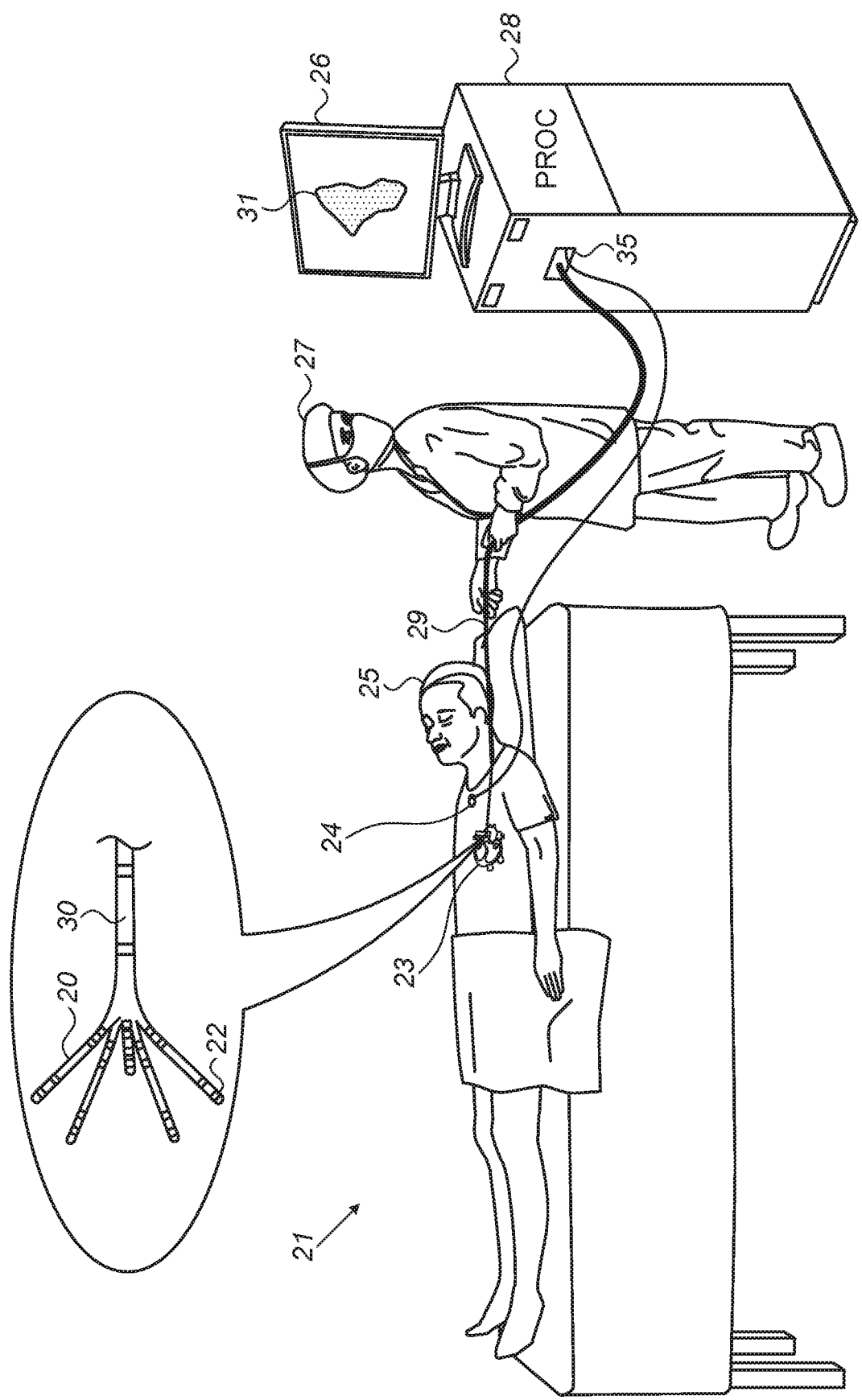
FIG. 1 is a schematic, pictorial illustration of a system for anatomical mapping, in accordance with an embodiment of the present invention.

An interior of an organ of a patient, such as a cardiac cavity, can be mapped using a mapping catheter, which may utilize various sensors fitted at its distal end for mapping while being within the organ. Using location signals that the various sensors generate, a processor may calculate the locations of the various sensors, such as the locations of sensing-electrodes, within the organ (e.g., the cavity). Using the calculated locations, the processor may further derive an anatomical map of the cavity. The process above may generate accurate maps of the cavity, yet requires a relatively large amount of time to complete.

Embodiments of the present invention that are described herein provide improved systems and methods for anatomical mapping of cardiac cavities. The disclosed techniques reduce the mapping time significantly by repeatedly adding to the map "internal volumes" during a mapping process. The "internal volumes" are inner volumes that are confined between the catheter's sensors (i.e., an inner volume that is confined within a distal-end assembly) and are therefore highly unlikely to contain tissue. As such, these volumes can be regarded with high likelihood as an internal volume of the cardiac cavity, and may thus be added as a whole to a map in formation. By way of example, the disclosed method can use multi-electrode catheters like the Lasso® (i.e., that comprises a spiral guidewire section) or Pentaray® (i.e., that comprises a multi-ray section) catheters. The multiple sensing-electrodes disposed over such catheters have a geometry that confines an "internal volume," as shown below.

In some embodiments, an anatomical mapping system receives a plurality of signals from multiple sensors coupled to a catheter distal end (i.e., coupled to the distal-end assembly), such as from sensing-electrodes fitted to a spiral guidewire of a Lasso® catheter or those fitted to arms of a Pentaray® catheter. Based on the plurality of signals, a processor in the anatomical mapping system calculates the locations of the sensing-electrodes. Based on the calculated locations, the processor calculates a shape of a distal end of the catheter, such as the shape of the distal ends of the Lasso® or the Pentaray® catheters.

The processor then determines whether the shape of the catheter distal end is deformed or not (i.e., has the unperturbed shape of a freely moving distal end, or not). A distal end may be deformed, for example, due to being in contact with a surface of the cardiac cavity (i.e., having a mechanical contact between the distal-end assembly and a surface of the organ). There are numerous methods for the processor to determine whether the distal end is deformed or not, where by way of example, two are described herein for two specific catheters:

(a) In an embodiment, the processor determines whether the Lasso® catheter is deformed or not by checking the planarity of disc surfaces that the spiral arms of the Lasso® catheter encompass, as elaborated below.
(b) In an embodiment, the processor determines whether the Pentaray® catheter is deformed or not by checking the planarity of surfaces that any two neighboring arms of the Pentaray® catheter may define.

If the processor determines that the shape of the catheter is deformed, then the processor adds only the shape of the distal end (e.g., the contour of the Lasso® guidewire or the contours of the Pentaray® arms) to the anatomical map (i.e., the processor is updating the anatomical map to denote only at least part of an external surface of the distal-end assembly as belonging to the interior of the organ). If, on the other hand, the processor determines that the shape of the distal end is not deformed, then the processor calculates an "internal volume," (i.e., volume of blood situated between the measured locations of electrodes). The processor then adds the entire calculated three-dimensional "internal volume" (i.e., inner volume) to the anatomical map of the cavity. In other words, the processor is denoting the inner volume of the distal-end assembly as belonging to the interior of the organ only when the distal-end assembly is not deformed.

In an embodiment, the processor calculates such "internal volume" by interpolating between the measured locations of the sensing-electrodes.

Since a mapping catheter typically spends the majority of mapping-time being not deformed (i.e., freely in the blood pool of a cardiac cavity), mapping internal volumes as disclosed herein is highly efficient. The processor typically repeats the process of adding internal volumes as the catheter moves through multiple positions within the cavity, so as to rapidly converge to a full volumetric map of the cavity. The terms 'location' and 'position' are used interchangeably in the description, meaning the same.

The disclosed technique has a distinct advantage that is can greatly shorten the time needed to obtain an anatomical map of a cavity. The shorter duration can improve the accuracy of the map and potentially simplify the clinical procedure involved in acquiring and using such map. Moreover, as a result of the filling with "internal volumes," the disclosed technique produces a representation of a cavity having reduced occurrences of artificial voids in the map. Such a representation better visualizes the reality of a void-less, continuous anatomy, which is harder to achieve otherwise.

System Description

FIG. 1 is a schematic, pictorial illustration of a system for anatomical mapping, in accordance with an embodiment of the present invention. As seen, a physician 27 is using an electro-anatomical catheter 29 to perform anatomical mapping of a heart 23 of a patient 25. Catheter 29 comprises, at its distal end, a Pentaray® mapping catheter that has five arms 20 to each of, are coupled one or more sensing-electrodes 22. A distal end the catheter comprises a magnetic sensor 30. During the mapping procedure, magnetic sensor 30 generates signals indicative of the position and orientation of the distal end of the Pentaray® catheter within a cavity.

Electrodes 22 acquire and/or inject signals indicative of their locations in heart 23. A processor 28 receives the magnetic and electric signals via an electrical interface 35, and uses information contained in these signals to calculate a shape of the distal end of the Pentaray® catheter. In some embodiments, the calculated shape is refined by processor 28 based on calculation that takes into account physical constraints derived from the known geometry of the catheter (e.g., known geometrical shape of the distal-end assembly), such as distances between neighboring electrodes.

In some embodiments, processor 28 updates an anatomical map 31 of a cavity of heart 23 with the reconstructed shape of the distal end. In some embodiments of the present invention, processor 28 construct anatomical map 31 in a rapid manner, by filling entire volumes of the cavity confined within the reconstructed shape. During and/or following the procedure, processor 28 may display anatomical map 31 on a display 26.

In some embodiments, as noted above, processor 28 receives signals from magnetic sensor 30 in response to magnetic fields from external field generators (not shown), for the purpose of measuring a respective precise location in three dimensions (x, y, and z axes) and orientation (roll, yaw, pitch) of the catheter distal end in the heart. The magnetic field generators are typically placed at known positions external to patient 25, e.g., below the table on which the patient is lying. The position signals are indicative of the position of sensor 30 in a coordinate system of the anatomical mapping system.

The method of location and orientation sensing using external magnetic fields is implemented in various medical applications, for example, in the CARTO™ system, produced by Biosense Webster Inc. (Ervine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In alternative embodiments, during the procedure the respective individual locations of electrodes 22 are tracked using an Advanced Current Location (ACL) technique. In the ACL technique, a plurality of external electrodes 24 are coupled to the body of patient 25; for example, six external electrodes 24 may be coupled to the patient's chest, and another three external electrodes may be coupled to the patient's back. (For ease of illustration, only one external electrode is shown in FIG. 1.) While electrodes 22 are inside heart 23 of the patient, electric currents are passed between electrodes 22 and external electrodes 24. Based on the ratios between the resulting current amplitudes measured at external electrodes 24 (or between the impedances implied by these amplitudes), and given the known positions of extremal electrodes 24 on the patient's body, processor 28 calculates a location of each of electrodes 22 within the patient's heart. The processor may thus associate any given impedance signal received from electrodes 22 with the location at which the signal was acquired.

The ACL technique of tracking electrodes locations is implemented in various medical applications, for example, in the CARTO™ system, produced by Biosense Webster Inc. (Irvine, Calif.) and is described in detail in U.S. Pat. Nos. 8,456,182, 7,756,576, 7,869,865, 7,848,787, and 7,848,789, whose disclosures are all incorporated herein by reference.

The example illustration shown in FIG. 1 is chosen purely for the sake of conceptual clarity. Other type of sensing geometries, and in particularly that of the Lasso® mapping catheter (produced by Biosense Webster, Inc.) may also be employed. In general, processor 28 may be embodied as a single processor, or as a cooperatively networked or clustered set of processors. Processor 28 is typically a programmed digital computing device comprising a central processing unit (CPU), random access memory (RAM), non-volatile secondary storage, such as a hard drive or CD ROM drive, network interfaces, and/or peripheral devices. Program code, including software programs, and/or data are loaded into the RAM for execution and processing by the CPU and results are generated for display, output, transmittal, or storage, as is known in the art. The program code and/or data may be downloaded to the computer in electronic form, over a network, for example, or it may, alternatively or additionally, be provided and/or stored on non-transitory tangible media, such as magnetic, optical, or electronic memory. Such program code and/or data, when provided to the processor, produce a machine or special-purpose computer, configured to perform the tasks described herein.

Although the pictured embodiment relates specifically to the use of multi-arm Pentaray® mapping catheter, the Lasso® mapping catheter is equally fit for the above description, as explained below. Moreover, other types of catheter distal ends may fit, such as that of a basket or that of a balloon.

Fast Anatomical Mapping Using Volume Filling

FIGS. 2A and 2B show volume rendered maps of cavity anatomy mapped by Lasso® and Pentaray® mapping catheters, respectively, in accordance with embodiments of the present invention. An inset 55 on the left-hand side of FIG. 2A schematically illustrates a Lasso® catheter comprising a lasso guidewire 42 to which multiple sensing-electrodes 22 are fitted.

As seen, a magnetic sensor 30a is fitted at a base segment of the catheter distal end. The Lasso® catheter is shown in inset 55 at its free-space configuration (i.e., not deformed). The Lasso® catheter was used for mapping tissue shown in FIGS. 2A(I) and 2A(II). Both figures show a resulting mapping of a portion of a cavity at a given position of the Lasso® catheter within a cavity of a heart 23. FIG. 2A(I) and FIG. 2A(II) were compiled from location data acquired when the catheter was positioned within the cavity blood pool and off the cavity surface, such way that Lasso® catheter was not deformed by contacting a surface of tissue.

FIG. 2A(I) shows the resulting cavity mapping as obtained without the disclosed technique. As seen, a mapped shape 52 is limited to locations over the spiraling lasso guidewire 42, in vicinity to sensing electrodes 22 (i.e., to a portion of volume of cavity that is largely following the shape of the distal-end assembly of the catheter).

In an embodiment, shape 52 is calculated by processor fitting a computer model of a shape of the Lasso® catheter distal end to the respective locations. In another embodiment, the shape is calculated by processor 28 interpolating over at least part of the measured locations. Whatever the calculation method is, no information is provided about a volume 51 that lasso guidewire 42 confines. FIG. 2A (II) shows an embodiment of the present invention, in which processor 28 derives confined volume (i.e., inner-volume) based the electrode locations it calculated the same way as with FIG. 2A(I). As seen, substantial confined volume 50 filling is achieved. Confined volume 50 is derived in addition to the shape of the catheter distal end, while the derived shape (that would wrap the distal end structure) is not shown in FIG. 2A (II) for clarity.

An inset 57 of FIG. 2B(I) schematically illustrates a Pentaray® catheter comprising a multi-ray 43 structure to which sensing-electrodes 22 are fitted. As seen, a magnetic sensor 30b is fitted at a base segment of the catheter distal end. The Pentaray® catheter is shown in its free-space configuration (i.e. not deformed by contacting a tissue surface). The Pentaray® catheter was used for mapping tissue shown in FIG. 2B(I) and FIG. 2B(II), which were compiled when Pentaray® catheter was positioned in a blood pool of a cavity of a heart 23 (i.e., where Pentaray® catheter was not deformed). FIG. 2B(I) shows cavity mapping obtained without the disclosed technique. As seen, a mapped shape 62 is limited to wrapping locations over the five arms of multi-ray 43 structure, in vicinity to sensing-electrodes 22.

In an embodiment, shape 62 is calculated by processor 28 fitting a computer model of a shape of the Pentaray® catheter distal end to the respective locations. In another embodiment, the shape is calculated by processor 28 interpolating over at least part of the measured locations. Again, whatever the calculation method is, no information is provided about a volume 61 that multi-ray 43 structure confines.

On the other hand, with the present invention, as seen in FIG. 2B(II), a substantial 'pentagonal pyramid'-like blood volume filling 60 is achieved by processor 28 performing a series of calculations similarly to these as described above.

To achieve the volume filling seen in FIGS. 2A(II) and 2B(II), a processor, such as processor 28, may, in an embodiment, interpolate between calculated sensor locations, a respective blood volume confined between multiple electrodes 22. Processor 28 may employ other calculations for calculating a confined volume of a cavity, based for example, on a geometrical model of the catheter that processor 28 stores.

The example illustrations shown in FIGS. 2A and 2B are chosen purely for the sake of conceptual clarity. Other volume capturing catheters may utilize the disclosed method, for example, a basket and balloon catheter distal ends. The distal ends of such catheters are typically convex, so that the internal volume confined therein is well defined.

In an embodiment, processor 28 is configured to determine whether the distal end of the Lasso® catheter is not deformed or deformed by calculating disc-like shaped surfaces encircled by a sub-set of sensors and checking if the calculated surfaces comprise a plane in space (e.g., follow an equation in the form of $Ax+By+Cz+D=0$, where x,y, and z are spatial coordinates, and A, B, C, D are real numbers) or not, respectively.

For checking the planarity (i.e., verifying whether a surface associated with the distal-end assembly is planar), the processor fits a general surface using a sub-set of electrode locations as a boundary condition. If the resulting surface fits an equation of a plane in space, as described above, to a certain accuracy, then the processor determines that the part of the distal end carries the respective sub-set of sensing electrodes is not deformed. The process moves to check another sub-set of electrodes that can generate the required boundary conditions, and check the linearity of the surface it created, and so forth, until the entire structure of the distal end is checked.

In a similar manner, of using sub-sets of sensing electrodes to establish boundary condition, in an embodiment, the processor determines if the Pentaray® catheter is deformed or not by checking the planarity of surfaces that any two neighboring arms of the Pentaray® catheter may define.

In an embodiment, processor 28 is configured to determine two or more neighboring arms of the Pentaray® catheter that are not deformed and accordingly update map 31 with a triangular area confined between the neighboring arms.

In another embodiment, processor 28 is configured to determine whether one or more arms of distal end of the Pentaray® are deformed or not based on identifying geometrical flexion of the arms. Such flexion may be identified by causing one or more deviations from expected angles between arms and/or causing a deviation from expected angle between an arm and the catheter shaft and/or causing a deviation from linearity of an arm. Techniques of this sort are described, for example, in U.S. patent application Ser. No. 15/610,865, filed Jun. 1, 2017, entitled "Using a Piecewise-Linear Model of a Catheter Arm to Identify Contact with Tissue," which is assigned to the assignee of the present patent application and whose disclosure is incorporated herein by reference.

In an embodiment, processor 28 is configured to determine whether a distal end is deformed or not based on one or more indications from contact force sensors. Generally, any suitable type of contact sensor or contact sensing method can be used.

Any indication of contact with tissue and/or deformation of the distal end (i.e., of the distal-end assembly) will result in processor 28 reverting to mapping a respective volume without using the disclosed technique.

Figure 3:
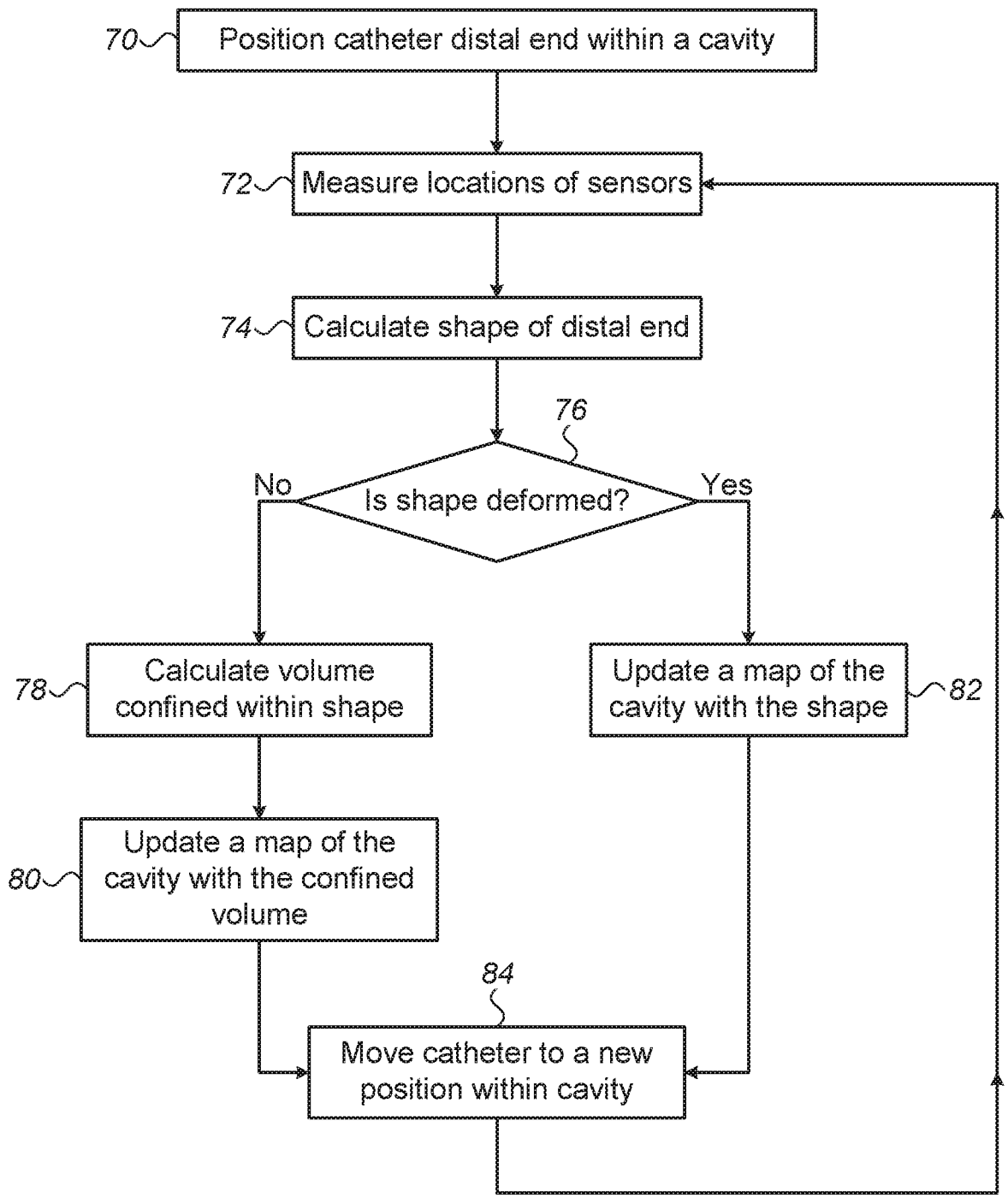
FIG. 3 is a flow-chart that schematically illustrates a method for anatomical mapping of a cardiac cavity, in accordance with an embodiment of the present invention.

FIG. 3 is a flow-chart that schematically illustrates a method for anatomical mapping a cardiac cavity, in accordance with an embodiment of the present invention. The procedure may begin with physician 27 inserting and positioning mapping catheter 29 into a cavity of heart 23, at a positioning step 70.

Next, at a measuring step 72, processor 28 acquires location signals, for example as generated by magnetic sensor 30, or by sensing impedances through electrodes 24. Based on the location signals, processor 28 calculates the locations of electrodes 22 within the cavity, and followingly derives the shape of the distal end of catheter 29, at a calculation step 74. In an embodiment, the derivation of the catheter shape is performed by interpolating between the measured locations of electrodes 22.

At a checking step 76, processor 28 compares the resulting shape of the catheter distal end with a known unperturbed shape of the catheter distal end (e.g., with a computer model of the distal end). If processor 28 finds that the derived shape is not deformed, processor 28 calculates a respective volume that is confined by the locations of electrodes 22, at a calculation step 78. Processor 28 updates anatomical map 31 accordingly, at an updating step 80, with the confined volume (i.e., "internal volume"), which the processer derived as explained above. The updating may or may not include also adding the shape of catheter distal end.

If, on the other hand, processor 28 finds the derived shape of the catheter distal end to be deformed, processor 28 updates anatomical map 31 only with the deformed shape of the distal end itself, at a mapping step 82. In the small fraction of the mapping time when the catheter does engage tissue, no assumptions regarding the existence of a confined volume are made, so no risk of mapping a tissue as blood is taken.

The method may then loop and return to step 72, at a moving step 84, when physician 27 moves the catheter to a new position so as to map a different region of the cavity, until the physician finds anatomical map 31 sufficient.

The example flow chart shown in FIG. 3 is chosen purely for the sake of conceptual clarity. In alternative embodiments other type of mapping-tools may be used. Additional information may be acquired and mapped parallel to locations, such as tissue type and an electrophysiological property of tissue.

Although the embodiments described herein mainly address pulmonary vein isolation, the methods and systems described herein can also be used in other applications, such as anatomically mapping any cavity in the body using a catheter geometry comprising an "internal volume." Although the embodiments described herein refer mainly to cardiac catheters, the disclosed techniques can be used with any other suitable medical probe in any other suitable organ.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
receiving one or more signals indicative of a position of a distal-end assembly of a medical probe within an organ of a patient;
based on the received signals, determining an inner volume that is confined within the distal-end assembly; and
updating an anatomical map of the organ to denote the inner volume of the distal-end assembly as belonging to an interior of the organ, wherein updating the anatomical map comprises verifying whether the distal-end assembly is deformed, and denoting the inner volume of the distal-end assembly as belonging to the interior of the organ only when the distal-end assembly is not deformed, and wherein, in response to detecting that the distal-end assembly is deformed, updating the anatomical map to denote only at least part of an external surface of the distal-end assembly as belonging to the interior of the organ.

2. The method according to claim 1, wherein determining the inner volume comprises calculating, based on the received signals, positions of one or more sensors coupled to the distal-end assembly, and deriving the inner volume from the positions of the sensors.

3. The method according to claim 2, wherein deriving the inner volume comprises calculating the inner volume based on the positions of the sensors and on a known geometrical shape of the distal-end assembly.

4. The method according to claim 1, wherein verifying whether the distal-end assembly is deformed comprises verifying whether a surface associated with the distal-end assembly is planar.

5. The method according to claim 1, wherein verifying whether the distal-end assembly is deformed comprises verifying whether an actual geometrical shape of the distal-end assembly deviates from a known un-deformed geometrical shape of the distal-end assembly.

6. The method according to claim 1, wherein verifying whether the distal-end assembly is deformed comprises identifying mechanical contact between the distal-end assembly and a surface of the organ.

7. An apparatus, comprising:
an electrical interface; and
a processor, configured to:
receive via the electrical interface one or more signals indicative of a position of a distal-end assembly of a medical probe within an organ of a patient;
based on the received signals, determine an inner volume that is confined within the distal-end assembly; and
update an anatomical map of the organ to denote the inner volume of the distal-end assembly as belonging to an interior of the organ, wherein the processor is configured to verify whether the distal-end assembly is deformed, and to denote the inner volume of the distal-end assembly as belonging to the interior of the organ only when the distal-end assembly is not deformed, and wherein, in response to detecting that the distal-end assembly is deformed, the processor is configured to correspondingly update the anatomical map to denote only at least part of an external surface of the distal-end assembly as belonging to the interior of the organ.

8. The apparatus according to claim 7, wherein the processor is configured to calculate, based on the received signals, positions of one or more sensors coupled to the distal-end assembly, and to derive the inner volume from the positions of the sensors.

9. The apparatus according to claim 8, wherein the processor is configured to calculate the inner volume based on the positions of the sensors and on a known geometrical shape of the distal-end assembly.

10. The apparatus according to claim 7, wherein the processor is configured to verify whether the distal-end assembly is deformed by verifying whether a surface associated with the distal-end assembly is planar.

11. The apparatus according to claim 7, wherein the processor is configured to verify whether the distal-end assembly is deformed by verifying whether an actual geometrical shape of the distal-end assembly deviates from a known un-deformed geometrical shape of the distal-end assembly.

12. The apparatus according to claim 7, wherein the processor is configured to verify whether the distal-end assembly is deformed by identifying mechanical contact between the distal-end assembly and a surface of the organ.

* * * * *